US008292797B2

(12) United States Patent
Chapman et al.

(10) Patent No.: US 8,292,797 B2
(45) Date of Patent: Oct. 23, 2012

(54) DIVERSIONARY THERAPY APPARATUS AND METHODS AND INTERACTIVE DEVICES

(75) Inventors: Ben Niall Chapman, Zillmere (AU); Sam Bucolo, Grange (AU); Glenn Smith, Zillmere (AU)

(73) Assignee: Diversionary Therapy Technologies Pty Ltd, Toowong, Queensland (AU)

( * ) Notice: Subject to any disclaimer, the term of this patent is extended or adjusted under 35 U.S.C. 154(b) by 965 days.

(21) Appl. No.: 12/090,448

(22) PCT Filed: Oct. 17, 2006

(86) PCT No.: PCT/AU2006/001531
§ 371 (c)(1),
(2), (4) Date: Sep. 3, 2008

(87) PCT Pub. No.: WO2007/045021
PCT Pub. Date: Apr. 26, 2007

(65) Prior Publication Data
US 2008/0319252 A1 Dec. 25, 2008

(30) Foreign Application Priority Data
Oct. 17, 2005 (AU) .............................. 2005905719

(51) Int. Cl.
*A61M 21/00* (2006.01)
(52) U.S. Cl. ........................................................ 600/27
(58) Field of Classification Search ............... 600/27–29
See application file for complete search history.

(56) References Cited

U.S. PATENT DOCUMENTS 5,190,285 A 3/1993 Levy et al.
(Continued)

FOREIGN PATENT DOCUMENTS
EP 0875821 11/1998
(Continued)

OTHER PUBLICATIONS

SK Seyrek, NL CorahL and LF Pace. "Comparison of three distraction techniques in reducing stress in dental patients." Journal of the American Dental Association, vol. 108, Issue 3 (1984):327-329.*

(Continued)

*Primary Examiner* — John Lacyk
(74) *Attorney, Agent, or Firm* — Workman Nydegger

(57) ABSTRACT

A diversionary therapy apparatus (100) provides a tangible intuitive and immersive interaction device for a patient so as to distract the patient from a treatment. It includes a handheld tablet device (110) having motion sensors and a screen (112) for showing digital content relating to a three-dimensional environment. A controller determines movement of the tablet device (110) and displays content on the screen (112) based on this movement so that the patient can interact with the three-dimensional environment displayed on the screen through physical manipulation of the device (110). Various other interactive features are also disclosed, including interchangeable selector elements, e.g. figurines (114), that may be mounted on the device (110) to allow selection of content and action, a camera, biometric sensors, a touchscreen, a domed rear surface to allow the device to rock on a surface and a profiled screen wall (124). Handgrips (122) may be provided skew to the horizontal to encourage immediate rotation of the device (110). Various other applications of the device are discussed, as is motion sensing based on a camera imaging a pattern on a marker element, e.g. on a figurine (114).

16 Claims, 10 Drawing Sheets

U.S. PATENT DOCUMENTS

| | | | |
|---|---|---|---|
| 5,453,758 A | 9/1995 | Sato | |
| 5,602,566 A | 2/1997 | Motosyuku | |
| 5,757,360 A | 5/1998 | Nitta et al. | |
| 5,918,603 A * | 7/1999 | Brown | 128/897 |
| 6,138,826 A * | 10/2000 | Kanamori et al. | 206/316.2 |
| 6,347,290 B1 | 2/2002 | Bartlett | |
| 6,573,883 B1 | 6/2003 | Bartlett | |
| 6,641,482 B2 * | 11/2003 | Masuyama et al. | 463/44 |
| 7,445,549 B1 * | 11/2008 | Best | 463/32 |
| 2003/0216176 A1 | 11/2003 | Shimizu et al. | |
| 2005/0063540 A1 * | 3/2005 | Hsiung | 380/217 |

FOREIGN PATENT DOCUMENTS

| | | |
|---|---|---|
| EP | 0971311 | 1/2000 |
| EP | 1 434 187 | 6/2004 |
| JP | 11299305 | 2/1999 |
| JP | 2004166995 | 6/2004 |
| WO | WO/99/08231 | 2/1999 |
| WO | 99/18495 | 4/1999 |
| WO | WO 00/57975 | 10/2000 |
| WO | 03/025730 | 3/2003 |

OTHER PUBLICATIONS

Hoffman, Hunter G., t al. "Virtual reality as an adjunctive pain control during burn wound care in adolescent patients", pp. 305-309, PAIN, United States, 2000, 85/1-2, 305-309.

JP 2008-535843, Mail Date Nov. 22, 2010, Japanese Office Action.

EP06790392.2, Mail Date Oct. 14, 2011, European Search Report.

* cited by examiner

DIVERSIONARY THERAPY APPARATUS AND METHODS AND INTERACTIVE DEVICES

The present invention relates to diversionary therapy apparatus and methods, as well as to interactive apparatus of more general application.

An important aspect of medical procedures is the management of pain and stress, and this is mainly achieved through pharmacological analgesia.

Pain perception however also has a strong psychological component, and cognitive techniques have long been used in conjunction with analgesics so as to reduce pain and distress suffered by patients during medical procedures. Such techniques have included breathing exercises, reinforcement of positive behaviour, hypnosis, behavioural rehearsal and distraction therapy.

Distraction or diversionary therapy aims to distract a patient's attention during a treatment so as to provide pain relief. The distraction may take a number of forms, and may include listening to music or to a story, reading a book or watching a video.

In recent years, research has been conducted into the use of video games and virtual reality in pain reduction. A virtual reality system typically includes a head-mounted display (HMD), e.g. stereoscopic goggles, that blocks out the real world and provides views of the artificially-created world, and a joystick or the like to allow a user to control their movement through the virtual world. The highly immersive nature of the virtual reality experience has been found to provide an effective distraction from painful treatments, with results being better than when using standard well-known gaming machines, which do not provide the same level of immersion. Virtual reality therapy has also been found useful in the treatment of phobias and post-traumatic stress syndromes, with patients able to face their fears or a traumatising event in a controlled environment.

An aim of the present invention is to provide novel diversionary therapy apparatus and methods, which, in their various embodiments, may provide new and useful pain management capabilities.

Viewed from one aspect, the present invention provides diversionary therapy apparatus including a tablet device configured to be held and moved by a patient during a treatment, the tablet device having a housing in which are mounted a display screen for displaying digital content, a motion sensor for sensing movement of the tablet device, and a controller for determining movement of the tablet device through the motion sensor and for displaying digital content on the screen in accordance with the tablet device movement, the digital content defining a three-dimensional environment, wherein the controller allows the patient to interact with the three-dimensional environment. The tablet device and digital content are designed so that when a user interacts with the content through the tablet device, the user experiences a distractive effect from a medical treatment.

Viewed from another aspect, the present invention provides a method of providing diversionary therapy to a patient undergoing a treatment, including the steps of: providing a patient with a handheld tablet device having a display screen, providing digital content to the display screen, the digital content relating to a three-dimensional environment, monitoring movement of the tablet device produced by the patient, and altering the digital content provided to the screen based on the monitored movement of the tablet device, wherein the patient is able to interact with the three-dimensional environment by moving the tablet device, the interaction providing a distraction to the patient from the treatment.

The present invention provides distraction/diversionary therapy for alleviating the anxiety and pain of a medical treatment by providing an immersive interactive experience, whereby a patient can interact with a three-dimensional environment, e.g. a virtual world, through a motion-sensitive handheld tablet device. The device can provide a patient with an intuitive tangible control interface with which the patient is able to interact instinctively and immediately, e.g. merely through tilting, rotating and/or translating the tablet device in space.

It has been found through trialling in the hospital environment that the device is able to provide effective diversionary therapy that can reduce the pain and stress of a treatment, e.g. in paediatric burns treatment.

The apparatus contrasts with virtual reality equipment that has previously been considered. Virtual reality equipment can be complex and bulky, and can be difficult to implement in the confines of a busy treatment area. Also, virtual reality equipment can be difficult to use, and controls are not necessarily intuitive in nature. Furthermore, the apparatus of such systems, including for example the use of head-mounted displays, may be intimidating, may be viewed as part of the overall treatment apparatus, and may be claustrophobic in nature. Virtual reality systems may be particularly problematic in paediatric care due to the need for close focussing and the lack of sufficient development in the patient's visual system. Indeed, prolonged use of virtual reality devices is not recommended for young children, and may result in occular focal damage.

The present device moves away from the use of greater degrees of visual immersion in virtual reality environments, and provides a tablet device that is simply controlled and viewed, and provides a suitably immersive and interactive environment for the patient through a direct tangible and intuitive interface. The apparatus also contrasts with standard gaming machines, which again are not tailored for use in the treatment environment, and often require a deal of time to understand and master. Training is generally required with the virtual reality and gaming machines, and they generally require the intervention of a clinical staff member to assist a patient in their use.

The present invention may provide an intuitive non-threatening, easily-controllable device that may be immediately picked-up and used, and that a user can physically manipulate in order to explore and to otherwise interact with a three-dimensional environment. The device may act as a window onto the three-dimensional world, with the user moving through the world by rotating, tilting and/or translating the device.

The device may be designed so that patients need very little instruction in its use, and instead are able to investigate the various functionalities of the device themselves through experimentation. The device may be configured to provide visual and tactile prompts to its functionality, e.g. in its shapes and colours, and to encourage experimentation and thought as to how to interact with it.

The device may be generally circular in shape, as this is particularly conducive to manipulation, and a patient may hold the tablet device in their hands in a manner similar to that of a steering wheel. The device may include hand grips about its periphery. In one embodiment, the device may include a set of hand-grips that are skewed from the general horizontal orientation of the tablet device, e.g. as defined by the screen, such that when a patient picks up the device, they will naturally tend to rotate the hand-grips to the horizontal, and so will move the device, activate the motion sensor and immediately cause a displayed scene to alter.

The device may however take other shapes, including square, rectangular, general polygonal shapes and oval shapes. Also, the rear of the device may be shaped and/or include features to aid in its movement. The device may for example include a curved or domed rear-surface. This may allow a patient with limited physical ability to use the device on a surface, e.g. their lap, a tabletop, a bed or the like, by rocking the device on its rear surface. A domed portion of the device may be removable, and different shapes of dome may be provided, e.g. more or less elongate, so as to accommodate different users of the device or encourage different movements. Other aids in movement could also be provided, e.g. a roller or ball mechanism may be provided on the rear surface. The device may also be suspended, e.g. from guide wires or a support arm, which may for example be articulated and may connect with the device through a universal joint or the like.

The display screen may include a wall around its periphery, which may be proud of the screen's front face and may be contoured, e.g. may change its height profile along the periphery of the screen, so that when the screen is angled to the user, some of the screen may be obscured. This may encourage movement of the tablet device so as to view the blocked portions of the screened image.

The device motion sensor may take any suitable form, and the device may for example incorporate any suitable inertial measurement unit. It may use gyroscopes and/or accelerometers. The device may sense movement in three-dimensions, and may sense translations in three-axes as well as rotations about those axes. It may determine pitch, roll and yaw, and accelerations in three perpendicular axes.

The display screen may take any suitable form, and may be for example an LCD screen, e.g. a TFT screen. It may include a stereoscopic screen, so that the three-dimensional scenes displayed appear to be in physical three-dimensional space.

The display screen may also incorporate a touch screen, so as to provide a further way in which a patient may interact with the device. The touch screen may allow a patient to select an object in a scene, activate a function or allow for movement within the scene. It may take any suitable form, e.g. resistive, capacitive, infrared, surface wave acoustic or strain gauge.

The controller may take any suitable form, and may be a suitably programmed microprocessor with associated memory and video capabilities, and may run an appropriate operating system and applications. It may be a single unit, or may comprise a number of separate control units, e.g. a separate video processor, a separate motion processor and the like.

The content may provide a number of different types of interactive experience. It may provide a storybook or a game. It may allow for an exploration of a three-dimensional environment and may allow interaction with entities found in the environment. It may provide a look and find experience or a skills-based experience. It may be designed to hold interest over a number of visits, and may include a number of different chapters of a story, levels of a game or the like. A complementary storybook may be included with the tablet device or a set of selector elements or figurines, which a carer may read to the patient during use of the device.

In one embodiment, the device does not include control buttons. Other embodiments do allow buttons, although generally they are kept to a low number and are easily actuated, e.g. as touch pads. The buttons could for example be provided to reset the device's content to a start position, to zoom into and out of a scene on the display screen, or to provide an on/off feature. They could also provide other functions, including for example a selection action, e.g. to select an entity shown in the scene, e.g. that has been located within a particular area or target on the screen. The buttons may be content-specific, and may provide different functions for different loaded content.

The apparatus may include a tangible selector element or artifact, which may for example be in the form of a token or a figure, and which a patient may insert into an input, e.g. socket, of the tablet device so as to select content or an action, e.g. so as to select a particular story or game, to select a new chapter, scenario or level within a story or game, to select a new character or difficulty level, or so as to provide some other selection of content, e.g. content parameters or paradigms, e.g. a look and find game rather than a skills-based game. The selector element may also be used to control an action. For example, if the device is used to watch a video, the selector elements may be used to initiate fast forward or rewind features. The content selector may be seen as a physically embodied menu element that provides for a tangible menu. The apparatus may include a set of such elements that a patient may insert into the device by hand to select or change related content. The set of elements may relate to different chapters of a story or different levels of a game.

The selector element may be provided in a number of different ways, and may for example be shaped as a figurine with a suitable identifier on it. It could also take the form of a card or disc or some other shape. The use of physical elements to provide a selection function has advantages over on-screen menus and the like in that they are simple to use, and provide an extra degree of interaction and control to the user in an intuitive form.

In order to identify the selector element, it may have an identification element on it that is read by a reader in the device. This could be a pattern on the element or could be data stored in memory on the element, with data from the memory transmitted to the tablet device. The pattern might for example be optically, electrically or mechanically read, and could be in the form of a one or two dimensional bar-code, a conductive array, a pin array or a camera-readable pattern. The selector elements could also include a transmitter, e.g. an RFID tag, within it to transmit data to the tablet device.

The selector elements may merely provide identification data, e.g. of scenarios or characters already stored in the tablet device, or may provide data for generating the content, e.g. scenarios or characters. They may also provide computer code for running a scenario, game or the like.

In one preferred form, the selector elements include a plurality of figures that may be plugged into the tablet device, for example into a socket on the front face of the device. The figures may have a data element, such as a marker on its base, which the tablet device can read. The marker may be read by a camera, and the tablet device may include a light source, e.g. a LED, for illuminating the marker.

The selector element may be movable on the tablet device, and the tablet device may include a motion sensor for the selector element. Movement of the selector element could then provide an interaction with the device, e.g. to allow for movement or change of viewpoints in the three-dimensional environment displayed on the screen. A patient could therefore interact with the three-dimensional environment through both movement of the tablet device and movement of the selector element, e.g. figurine.

The device may include a camera. This may be used to capture digital images that may then be displayed on the screen, and may provide an augmented reality device, e.g. a device which superimposes or otherwise blends virtual features onto a real world image. The device may also process captured images to extract features and to initiate various functions based on the extracted features. For example, the camera may capture a marker on a selector element, and the device may process the image so as to determine the character or function that the selector element represents. The device may also process general images captured by the camera, e.g. to generate sounds or images or take an action based on features found in the captured pictures, such as edges, forms, patterns, colours and/or movement. Thus, tilting of the device may not only cause changes in the displayed scene due to the output of the motion sensors, but may also cause changes in the displayed scene due to changes in the images caught by the camera as the tablet device moves. The camera may for example be provided towards the top of the device. The tablet device may include controls to allow a user to select the images to capture.

The camera may provide a number of different functions, and may significantly increase the interaction and engagement of the patient with the device. The camera may be a still image camera or a video camera, and may for example be a web-camera. It may be mounted in any suitable location on the device. In one preferred form, the camera is provided on the front of the device facing the user. This allows the user to capture themselves on the screen easily. Also, the camera could be obscured if mounted on the rear side of the device if a user holds the device on their lap or the like.

The camera may form part of the motion sensing system for the device, and captured images may be processed for a marker or markers in the camera's field of view. The location or orientation of the markers may then be determined so as to determine the relative position of the camera and so of the tablet device itself to the markers. In one embodiment, a marker is provided on a marked and weighted object that is mounted on the device, e.g. in a gimballed manner. The object then remains in a vertical orientation a fixed distance from the camera as the device is rotated, so that the relative orientation of the object and the camera changes with the movement of the device. This change can be detected by processing the orientation of a marker on the object, so as to provide positional and movement information for the device. Where the above-mentioned selector elements are movable, the selector elements may have markers on them, and the camera may be used to image the markers. The orientation of the marker may then be used to detect movement of the selector elements.

The device may include biofeedback features. It may for example include a sensor for monitoring a physiological condition of the patient, for example heart-rate, blood pressure, brain activity, muscle tension, skin conductivity, respiratory rates, oxygen saturation and general biometrics and the like. The sensor output may allow a patient to interact with the device, e.g. to alter the digital content provided to the screen. The device may assist a patient in the control of their physiological response to a situation by providing a function that depends on the particular physiological state of the user or by providing a visualisation of the physical state. The device may for example include a heart-rate sensor, a temperature sensor, or a skin conductivity sensor. It may include an ECG (electrocardiogram), EEG (electroencephalogram) or EMG (electromyogram) device.

In one embodiment, the device may include a heart-rate sensor, e.g. mounted on hand-grip of the device, and the content may change based on the heart-rate, so as to encourage the patient to reduce their heart-rate, e.g. through a visualisation of the heart-rate and/or through the ability to take a desired action when the heart-rate matches set criteria.

The device may also provide haptic feedback to the user, e.g. a particular interaction may cause the device to vibrate or the like. Thus, the device may include a vibrational element, such as a vibration motor, that is vibrated in accordance with user interaction.

The device may include a sound sensor, e.g. microphone, for responding to surrounding sounds, and for causing the device to react to the sounds. The device may include a sound generator, including e.g. a microphone and/or earphones, for emitting sounds, e.g. narration, sound effects or the like to the patient. The device may include surround sound or spatialised audio apparatus to further increase the immersion into the environment.

The device may include a link to an external device, e.g. a digital content store or a controller or the like, e.g. to receive content and/or to provide processing support. The device could be connected to the external circuitry by a communications cable, and so be a tethered device, but is preferably a wireless connection. The device may for example use a Bluetooth™ or Wi-Fi connection or the like.

The device is preferably built so as to provide a degree of toughness associated with the needs of a treatment area, and preferably the housing is of a waterproof nature, so that a patient may utilise the device in a treatment bath or the like. For example, a burns patient may need to be treated whilst in a bath of water, and the device should be sufficiently waterproof as to prevent any problems. The device may also include suitable magnetic shielding when used in CT or MR scanning procedures or the like.

The device may include a mains power lead, but is preferably battery-powered, so that it is fully self-contained.

The device has application in many types of medical treatment, including in burns treatment, e.g. dressing of the burns, emergency medicine, oncology, radiology, dentistry and the like. It may be used by any age-groups, including adults, but is particularly useful for paediatrics care, and in younger children in the ranges of 1 to 7. The device may also be used in non-treatment environments, e.g. in pre-operative waiting, and may be used in the general medical setting.

The tablet device may also have wider application in the general entertainment and display device fields.

Viewed from another aspect, the present invention provides a handheld storyboard tablet device, the tablet device having a housing in which are mounted a display screen for displaying scenes from a story, a motion sensor for sensing movement of the tablet device, a memory for storing digital content relating to a story to be displayed, and a controller for determining movement of the tablet device through the motion sensor and for displaying scenes from said stored content in accordance with the tablet device movement. The device can include the various features discussed above, including for example the physical selector elements for selecting content or action, e.g. chapters or characters of the displayed story.

Various of the above features may also be used independently of a tablet device. Viewed from another aspect, the present invention provides an interactive display device including a housing, a display screen, a controller and a motion sensor for determining movement of the device, wherein the controller displays content on the screen in accordance with movement of the device. The device may be a tablet device with a display screen mounted on it or a head-mounted display that may have a pair of display screens, one for each eye. The device may include any of the above features, including for example the use of a set of interchangeable physical selector elements that can be attached to the display device to choose content and or to make other selections, e.g. as a replacement to a menu. The device may also include for example a camera for capturing images that may be processed to provide further interaction, e.g. through the use of the images in the displayed content or through the extraction of features from the images that may be used as triggers or control parameters for various functions.

The use of the camera to capture an image of a marker and to determine the relative orientation of the marker and the camera is another example of a feature that has general applicability. It could for example be used as a motion sensor in general in any suitable field of application, e.g. for gaming machines, head-mounted displays, and in any other positional-sensitive electronic product.

Thus, viewed from another aspect, the present invention provides a motion sensor including a camera and a marker element mounted together a fixed distance apart, the camera and marker element being relatively movable in their orientation to one another, and the camera being adapted to capture a pattern of said marker element. This allows images of the marker element taken by the camera to be processed to determine the orientation of the pattern of the marker element, and so the relative orientation between the two. Preferably, the camera is fixed in position and the marker element can change its orientation. The camera can be fixed to a device, such as a handheld tablet display device, and the marker element can be generally fixed in position or orientation, e.g. through being weighted, so as to remain vertical, or through being attached to a fixed anchor, e.g. a bracket or the like. Movement of the device, e.g. tablet device, will then change the relative orientation of the camera and marker element, and processing of the captured images will provide information on this change and enable suitable action to be taken, e.g. a change in the displayed scene.

This aspect of the invention may also be seen as providing a mounting device for a marker element, the mounting device including a support, a marker element moveably mounted on the support, the marker element being weighted so as to be biased to a rest orientation, and camera mount means for fixing the mounting device to a camera or camera mount, such that the support is held in fixed relationship to the camera.

The mounting device may be attached to a hand-held screen, may be incorporated into a head-mounted camera system, or may be provided in any device that is to be made motion-sensitive.

The mounting device may encapsulate the camera lens and the marker element in a single enclosure, which may include lighting, such as an LED light source, so as to provide a consistent illumination of the marker. As the marker element is weighted, it will be biased by gravity to a constant orientation. As the camera is moved, e.g. by moving the screen or head-mounted camera system, the relative orientation of the camera to the marker element surface, and hence the marker element pattern as seen by the camera, will change accordingly. From the varying images fed from the camera, a controller can calculate the orientation and take appropriate action, e.g. may modify a generated image accordingly so as to reflect the change in orientation.

The marker element may be pivotally located in a bore in the support, and may have a weight at its lower end. However, other forms of weighting or gravitational biasing may be used. The mounting device may have a cowl-like housing which at least partially shields the camera lens from ambient light. The marker element may be removably mounted on the support, so as to be exchangeable for other marker element, in which case the marker pattern may represent identification information or other information.

It should be noted that any one of the aspects mentioned above may include any of the features of any of the other aspects mentioned above and may include any of the features of any of the embodiments described below, as appropriate.

Embodiments of the present invention will now be described, by way of example only, with reference to the accompanying drawings. It is to be understood that the particularity of the drawings does not supersede the generality of the preceding description of the invention.

Figure 1:
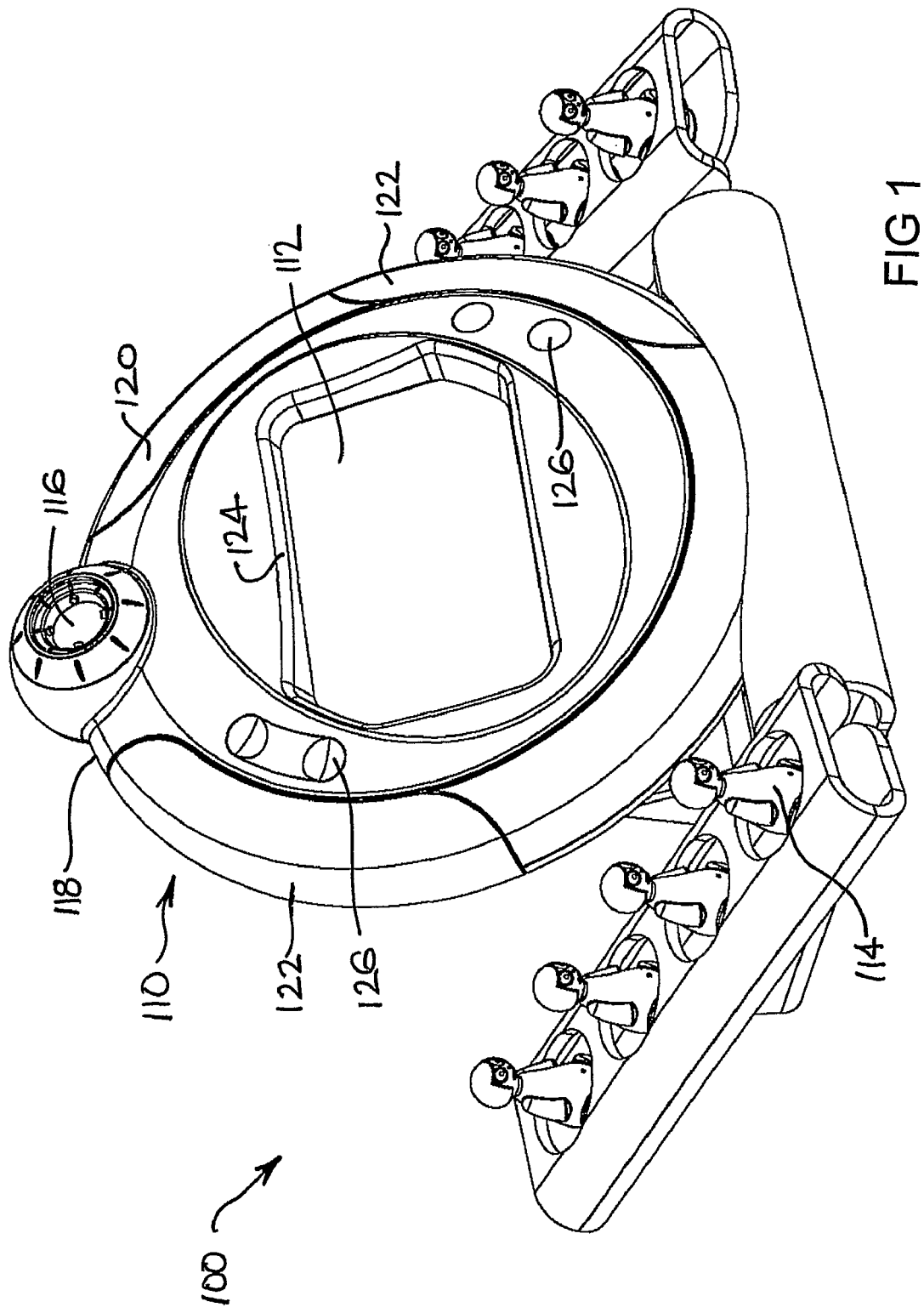
FIG. 1 is a perspective view of diversionary therapy apparatus in accordance with one embodiment of the present invention.
Figure 2:
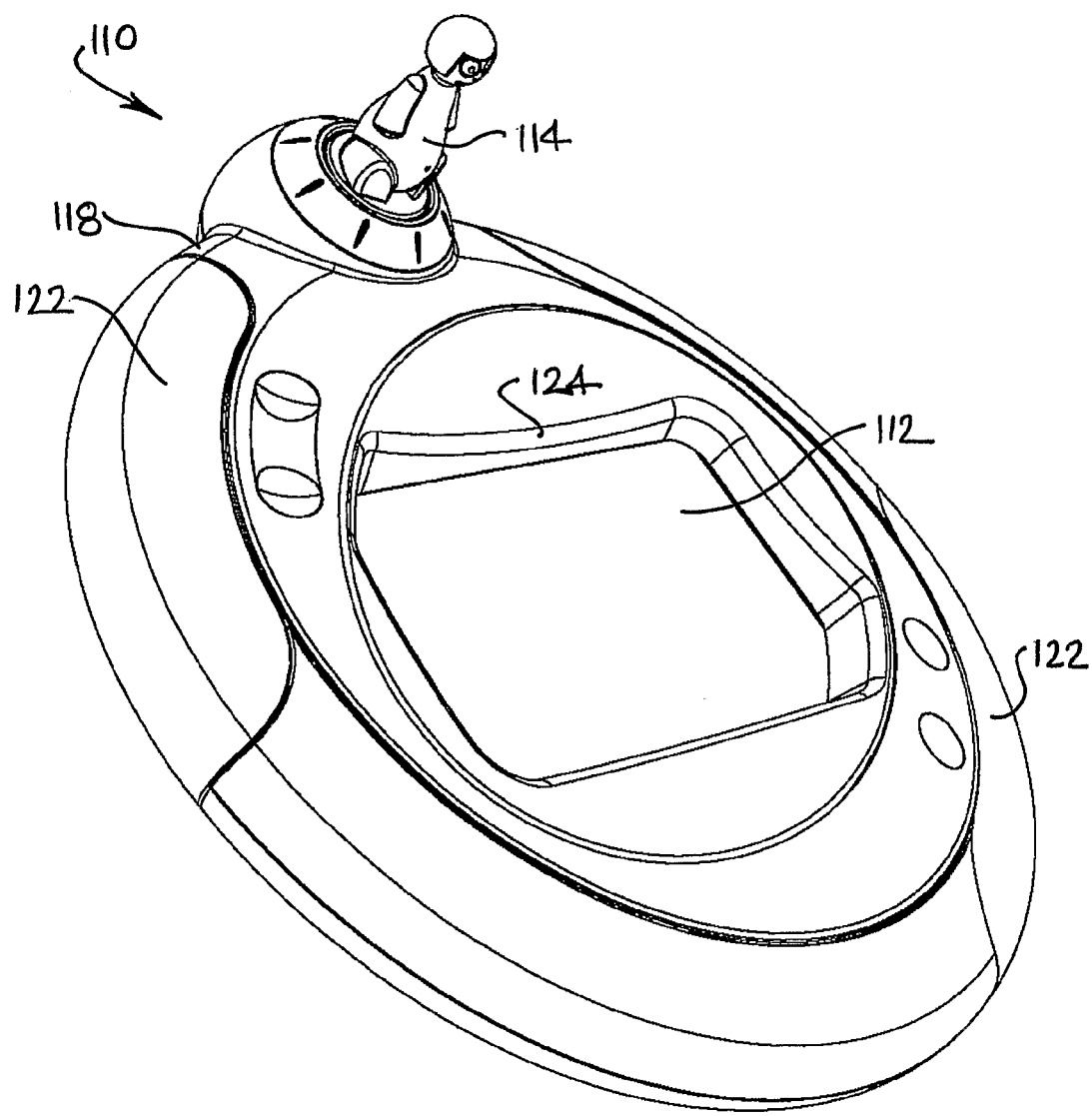
FIG. 2 is a side perspective view of the tablet device of FIG. 1 with a menu figure mounted thereon.

Referring to FIG. 1, diversionary therapy apparatus 100 includes a hand-held motion-sensitive tablet device 110 which acts as a tangible interface for allowing a user to interact with digital content displayed on its screen 112, and a set of figurines 114, which act as tangible content or menu selectors and allow a user to make various content and function choices by manually placing the appropriate figurine 114 into a socket 116 on the tablet device 110, e.g. as shown in FIG. 2.

Figure 3:
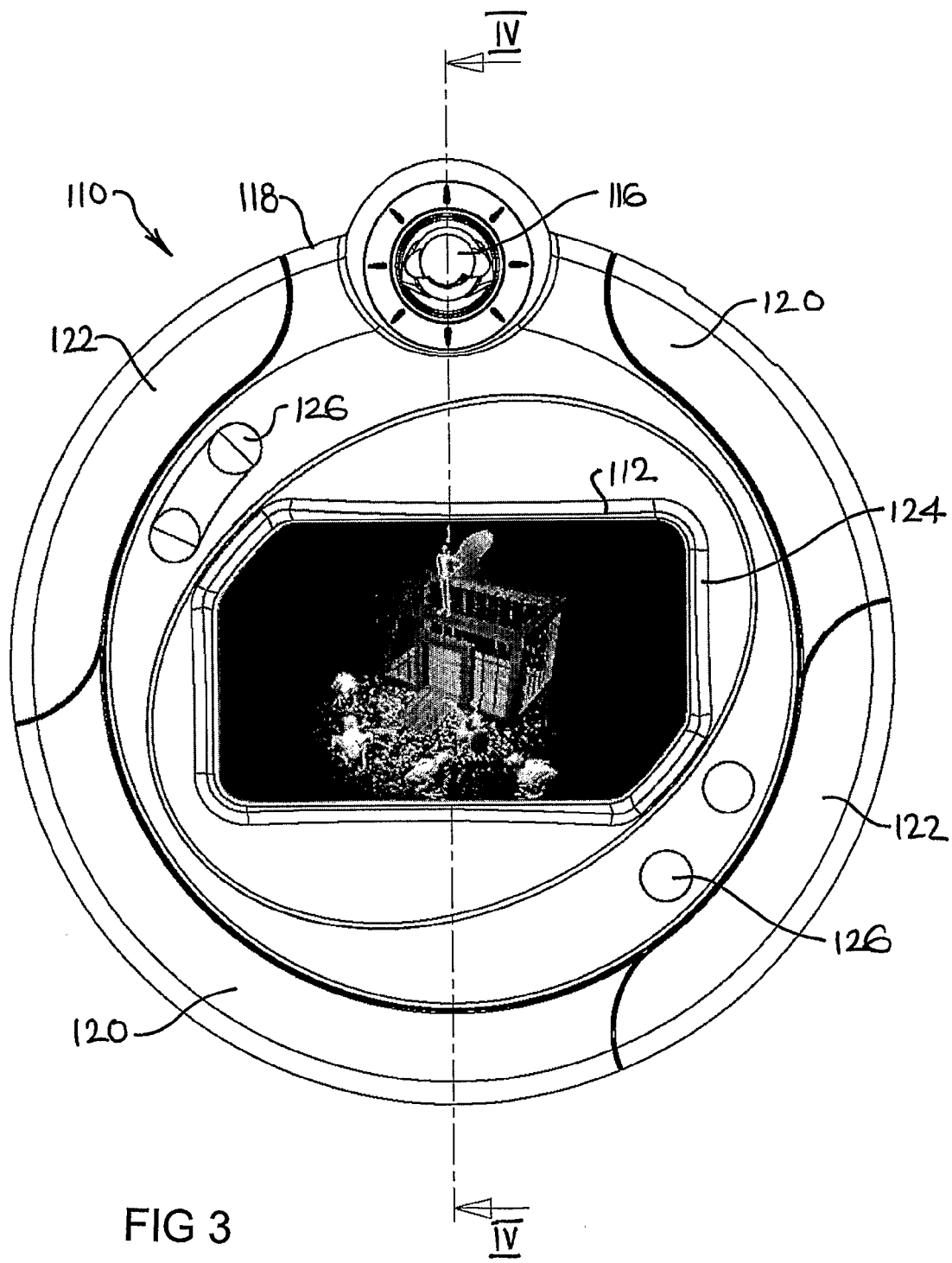
FIG. 3 is a front view of the tablet device of FIG. 2 showing digital content on the tablet device screen.

Once content is selected using a figurine 114, an appropriate three-dimensional scene is shown on the screen 112, as shown in FIG. 3, and movement of the device 110, e.g. tilting, rotating and/or translating the device, allows the user to interact with the scene, e.g. to move through the displayed three-dimensional environment and to interact with entities in that environment.

The device 110 can be used in a hospital environment, e.g. in a burns unit or the like, and may be given to a child to interact with whilst the child is undergoing treatment, e.g. a dressings change. The device 110 has been found to be effective in distracting a patient's attention from the treatment, and accordingly has been found to reduce the pain and anxiety felt by the patient.

The tablet device 110 and digital content are designed to provide an immersive experience for the user, and the device 110 allows the user to interact with the content in an intuitive and immediate fashion, without complicated controls or the like, and without any great need for assistance from clinical staff.

The tablet device 110 includes a circular housing 118 in the front of which is mounted the screen 112, which may be an LCD screen or the like. A hand grip area 120 is provided about the periphery of the housing 118, and a pair of main hand grips 122 are provided skew to the general horizontal axis of the device 110, e.g. as defined by the screen 112. The skew placement of the hand grips 122 prompts a user to immediately rotate the tablet device 110 as soon as they pick it up, until the hand grips 122 are in a horizontal orientation, i.e. they are aligned along a horizontal axis. This action immediately causes movement in the displayed content scenario, and allows a user to immediately interact with the device 110.

Also to encourage movement, the device 110 may include a contoured wall 124 around the periphery of the screen 112, which is proud of the screen 112 and varies in height, so as to obscure portions of the screen 112 at certain viewing angles. This can encourage a user to move the device 110 around, so as to be able to see the blocked parts of the scene.

The device 110 also includes buttons 126, in the form of touch pads, for allowing various functionality. A button may for example reset the displayed content to the start position, or could allow for zooming into or out of the displayed scene. The functions of the buttons may change depending on the content being displayed and the story or game or such like that is being provided. The buttons are arranged for simple activation using the thumbs, when a user is holding the handgrips 122.

In one embodiment, buttons are not provided, and for example the movement of the device 110 could provide such functionality through various specific tablet device movements that may be associated with a function. For example, translational movement of the tablet device in a forward or backwards direction could be a trigger for a zoom in or a zoom out, and a vigorous shake of the device could provide a reset.

Figure 4:
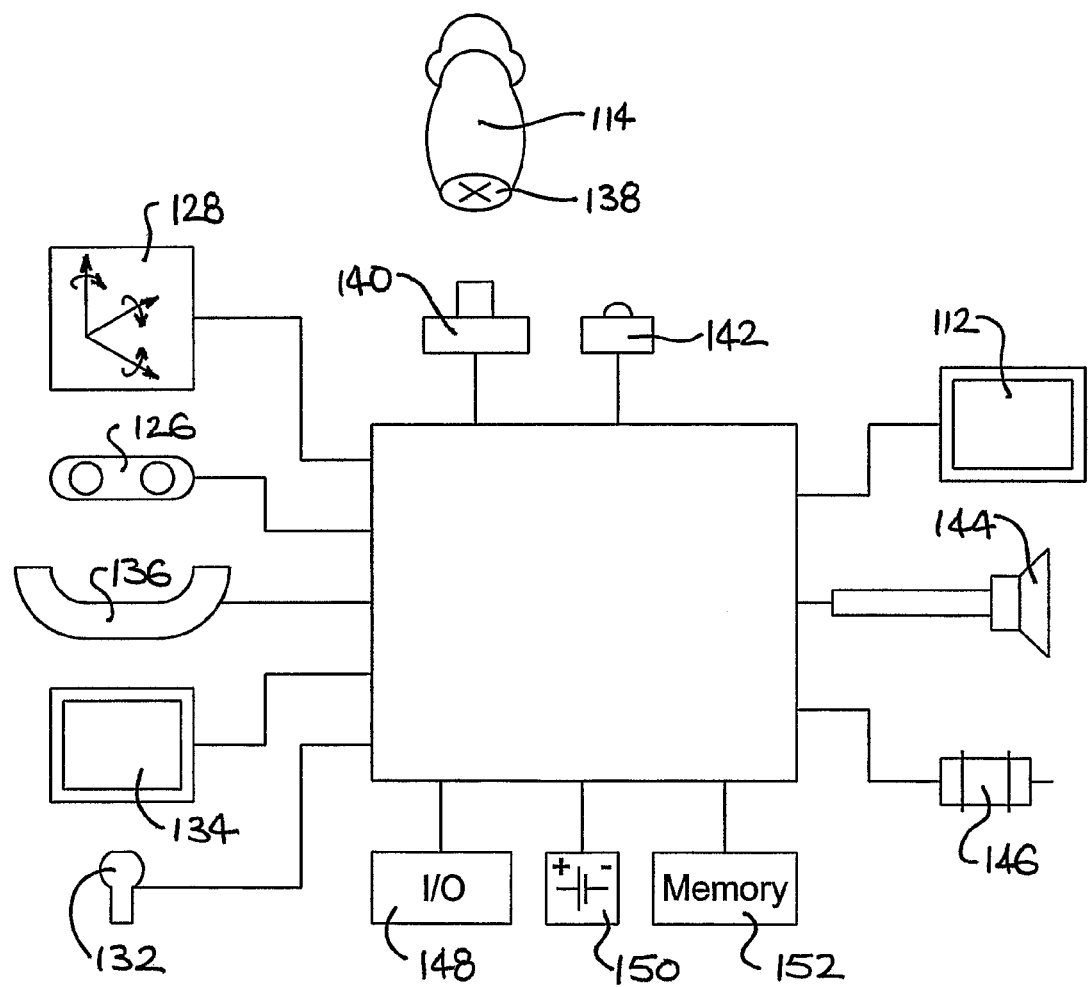
FIG. 4 is a block diagram of the tablet device system.

Referring to FIG. 4, the tablet device 110 houses a motion sensor 128, which may be a number of motion sensors, such as gyroscopes and/or accelerometers, and e.g. may be in the form of an inertial movement detector unit. The motion sensor 128 monitors the position and motion of the tablet device 110. The device 110 includes a controller 130 that determines the movement and position of the tablet device 110 from the output of the motion sensor 128 and that provides appropriate content to the screen 112 based on the determined motion.

The controller 130 will also receive other inputs for allowing further forms of interaction, e.g. from the touch pads 126. The various different types of interaction provide a user with further interest and immersion into the device. Other inputs could include a microphone 132 for detecting sound and a touch screen 134, e.g. mounted over the display screen 112. The touch screen 134 could be used for example to select features or directions in the three dimensional environment or for pressing soft buttons/activation regions on the screen or the like.

A further input may be from a physiological sensor 136. The physiological sensor 136 may take a number of forms, and could measure heart rate, blood pressure, brain activity, muscle tension, skin conductivity, respiratory rates, oxygen saturation, general biometrics, or the like. It could provide ECG, EEG or EMG information. The user may then interact with the content based on a control of a physiological condition, and the device may encourage a user to control the condition, e.g. by relating the condition to achieving a result or the like, or by visualizing the condition to the user. In one embodiment, the hand grips 122 may have ECG electrodes associated with them that monitor the user's heart rate, and the user may be rewarded if they lower their heart rate, e.g. by the device allowing the user to complete a task or change a view in the three dimensional environment.

The figurines 114 provide a tangible selection function, and may be recognised by the tablet device 110 in any suitable manner. For example, the figurines could have RFID tags mounted on them that are read by a reader in the device 110. Optically, electrically or mechanically readable patterns could also be used on the figurines 114, including one or two dimensional bar codes, a conductive array, a pin array or the like, and then could be read by an appropriate reader in the device.

Referring to FIG. 4, the figurines 114 may have marker patterns 138 on their bases, and the tablet device 110 may have a camera 140 and LED 142 mounted in the socket 116. The LED 142 lights the marker pattern 138 and the camera 140 captures an image of the marker 138. The captured image may then be processed using appropriate image processing software to identify the marker pattern 138, and the controller can take appropriate action dependent on the identity of the figurine, e.g. display content associated with the marker pattern, e.g. a particular character or chapter or level of a book or game or the like. The figurines may also allow for selection of functions, such as a fast forward or rewind of a video or the like.

As well as outputting content to a display 112, the tablet device 110 may also provide other outputs and stimuli. For example, it may provide an audio output, such as a narration, music, sound effects or the like, e.g. through a speaker 144, e.g. using a surround sound device, and may provide haptic feedback, e.g. through a vibrational motor 146, that will vibrate the device 110 under certain conditions, e.g. when a particular event occurs in a story or game.

The controller 130 may also include suitable input/output modules 148, which could include a wireless transceiver, a USB connection or the like. This may allow the device to download new content or the like, e.g. from a data carrier, a database, a network server or the like, and/or connect to external processing devices. The figurines 114 could also act as data carriers, and could provide data associated with a particular scenario or the like. For example, suitable memory could be mounted in the figurines that could be accessed via a transceiver or electrical connectors.

The device may be powered by rechargeable batteries 150, and may include memory 152 accessible by the controller 130 for storing digital content, applications, operating systems and the like.

The controller 130 may be a microprocessor or any other suitable processing element. It need not be a single unit, but could include a number of processing units, e.g. a separate graphics processor, motion processor or the like.

The camera 140 or a further separate camera may also be used to provide other types of interaction. For example, when the figurine 114 is not in place, the camera 140 may capture digital images that may be combined with other digital content and displayed on the screen 112. It may therefore provide an augmented reality device, in which real and virtual image data are combined together. Images captured by the camera 140 may also be processed to identify features within the image, e.g. shapes, colours, movement or the like, and these features may be used to interact with the device, e.g. to change the content displayed, sounds emitted and the like. This may provide further levels of interaction, and movement of the device may cause interactions through both the movement of the device itself and a resulting sequence of images that are captured by the camera during the movement. Images may be user-selectable, e.g. by showing the camera image on the screen 112 and by capturing the image when one of the touch pads 126 is pressed.

The camera 140 may be a still camera or video camera, and may be a web camera. It may be mounted to face forwardly of the tablet device 110, as shown, and may be mounted towards the top of the device. The same camera need not be used to both sense the figurines 114 and provide the above further interactions, and a further camera could be provided for this.

Figure 5:
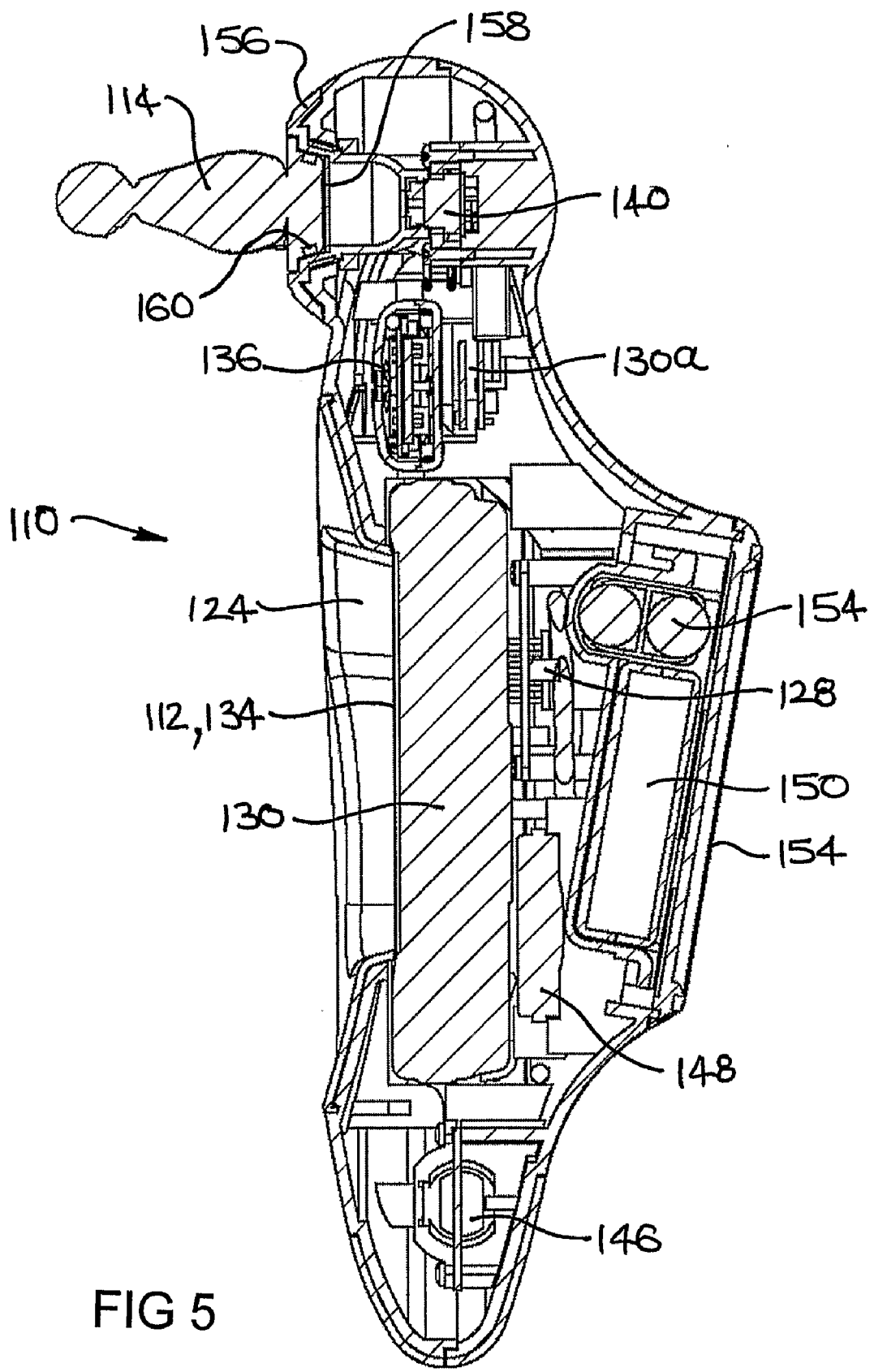
FIG. 5 is a cross-sectional view through line IV-IV of FIG. 3.

FIG. 5 is a cross-section through the tablet device 110, and shows a possible arrangement of various parts of the device. It also shows the device having a rubber foot 154 for placing on a surface when not in use. In the shown embodiment, the screen 112, touchscreen 134 and a main processing unit 130 are provided in the same subunit and a pre-processor 130a is used to pre-process signals from the motion sensors 128 before passing them to the main processor 130. Such arrangements are not however necessary, and for example the processors may be combined together, and the display screen may be separate from the processors.

The camera 140 includes a focussing ring 156 and a protective lens 158, and the figurines 114 may be held in place by magnets 160.

Figure 6:
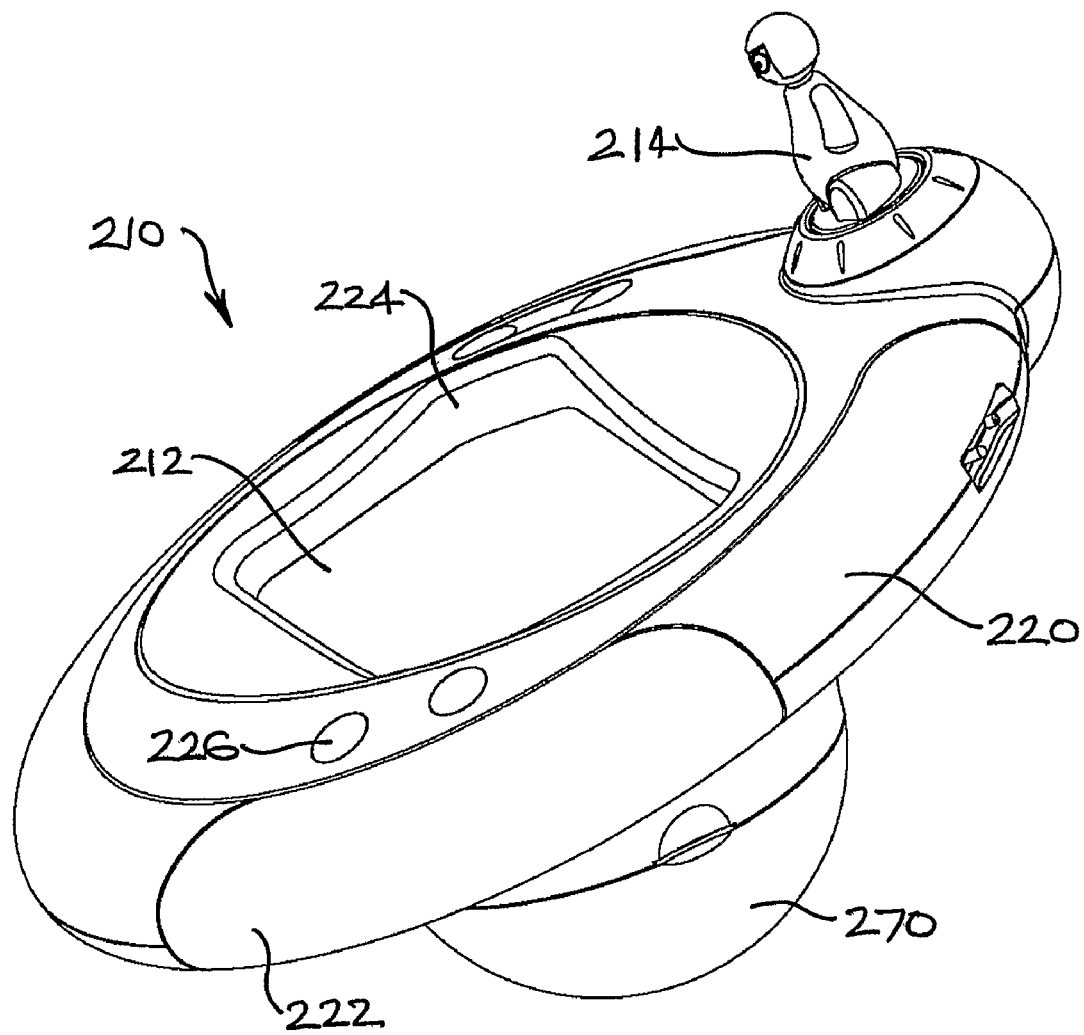
FIG. 6 is side perspective view of a second embodiment of the present invention, the tablet device including a domed rear portion.
Figure 7:
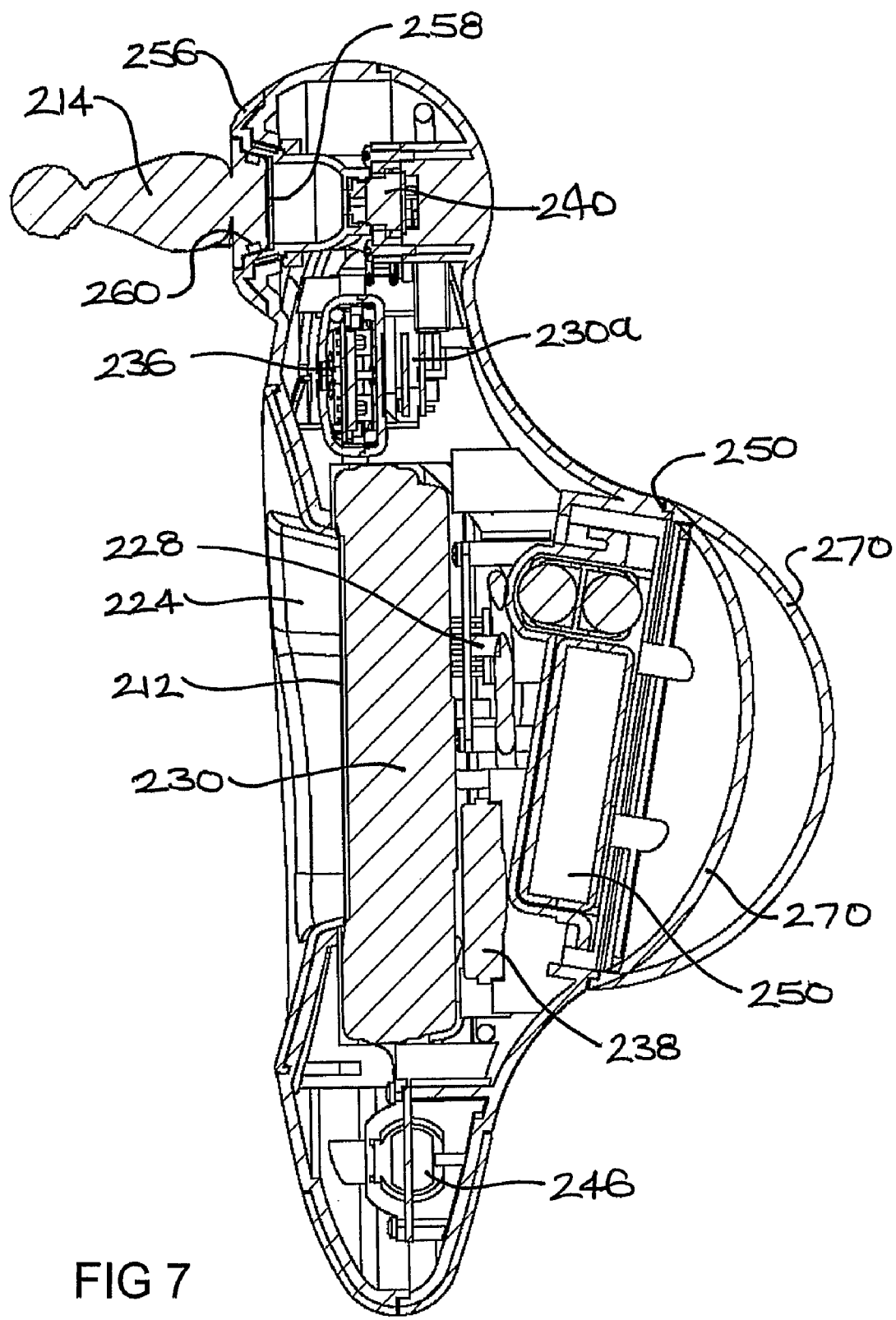
FIG. 7 is a cross-section through the centre of FIG. 6.

FIGS. 6 and 7 show a further embodiment, which is similar to the first embodiment, and similar elements to the first embodiment are numbered the same, but with an additional hundred added to them. The device 210 includes a domed rear portion 270 in place of the rubber foot 154. This domed portion 270 allows a user to roll the tablet device 210 on a surface, e.g. a tabletop, a bed or a patient's lap, and so assists a user who may have limited physical abilities. The domed rear portion 270 may be provided as an add-on to the basic tablet device of the first embodiment, and a number of different dome shapes could be provided, e.g. more or less elongate.

Instead of the domed surface 270, the device could be provided with a roller or ball attachment. Also, the device could be suspended on a boom. It could be mounted by guide wires or on a support arm, and for example could be attached to an articulated arm, e.g. via a universal joint.

Figure 8:
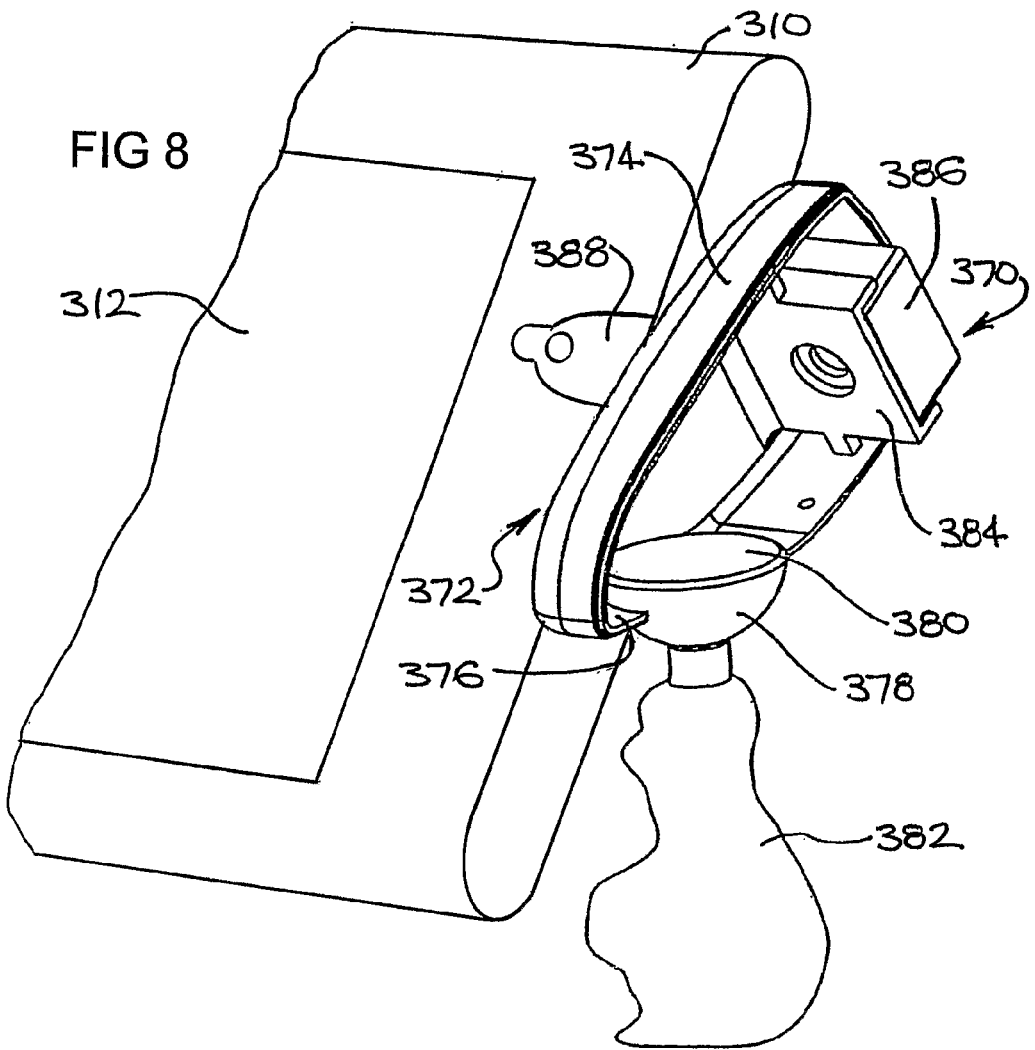
FIG. 8 is a partial sectional perspective view of a motion sensor and tablet device according to another aspect of the present invention.
Figure 9:
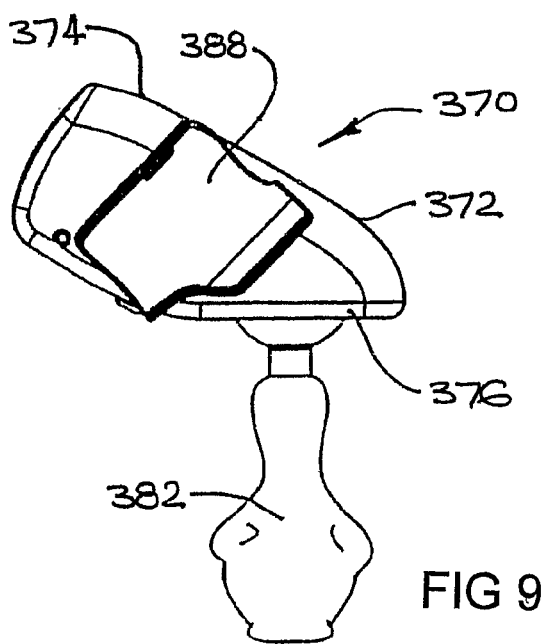
FIG. 9 is side view of the motion sensor portion of FIG. 8.
Figure 10:
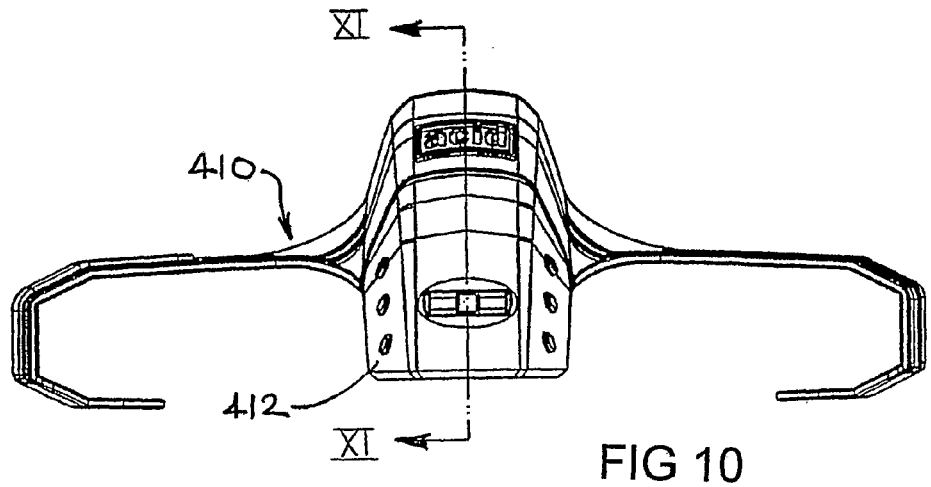
FIG. 10 is a front view of a portion of a head-mounted motion sensing device incorporating a motion sensor according to another embodiment of this aspect of the invention.
Figure 11:
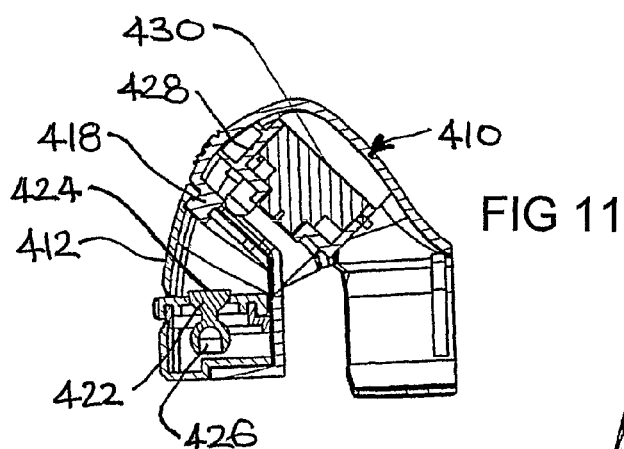
FIG. 11 is a sectional side elevation of the device of FIG. 9 through line XI-XI.

FIGS. 8 and 9 show another embodiment of the device which uses a rectangular tablet device 310 having a screen 312, and an alternative type of motion sensor 370 that may be used by itself or with other motion sensors also.

The motion sensor 370 includes a marker mount 372 comprises a cowl-like housing 374 having a support 376 for a marker element 378, e.g. a modified figurine. The support 376 is in the form of a plate having a circular aperture or bore within which sits a marker element 378 having a hemispherical body. This simple arrangement provides an effective gimbal mount which gives the marker element 378 rotational freedom about two perpendicular axes parallel to the support plate 376, as well as rotational freedom about an axis perpendicular to the support plate 376. However, it will be appreciated by those skilled in the art that other constructions may be used to mount the marker element 378 pivotally in the support 376, such as various types of gimbal mounts.

Suitably, friction between the body of the marker element 378 and the support 376 is reduced to a level which does not hinder pivotal movement of the marker element 378 within the support 376. In a modified embodiment, the support plate 376 is located around the neck of the marker element below the hemispherical body. In other words, the mount comprises a marker element having a neck portion located in a bore in a support plate, the neck portion being surmounted by a head portion having a rounded underside to enable the neck portion to swing like a pendulum about at least two perpendicular axes.

The marker element 378 has a flat upper surface 380 on which a unique identifying pattern is provided. A weight 382, e.g. a body portion of a figurine, depends from the marker element 378, and biases the marker/weight combination to a generally vertical orientation (so that the marker surface 380 is generally horizontal). However, it will be apparent to those skilled in the art that the marker surface 380 does not have to be horizontal. It is sufficient that the weight 382 biases the marker surface 380 to a constant orientation relative to the horizontal.

The weight 382 is preferably shaped as a handle which can be grasped by a user.

The marker mount 372 also includes a camera mount 384 for a camera 386, e.g. a web camera. In this manner, the camera 386 is fixed relative to the housing 374 and the support 376.

The maker 378 and camera 386 are preferably positioned relative to each other so that the marker surface 380 is at or near the focal plane or region of the camera 386.

The marker mount 372 also includes a clip-like attachment 388 to permit the maker mount 372 to be attached to the handheld device 310.

In use, the image on the marker surface 380 is captured by the camera 386 and fed to a processor where the image is recognised, and corresponding content, e.g. graphics, is generated. If the user moves the display screen 310 relative to the weighted handle 382, there will be relative movement between the screen 310 and the marker 378, and hence relative movement between the camera 386 and the marker surface 380. For example, if the screen is tilted relative to the weighted handle 382, the marker surface 380 will tilt relative to the camera 386. If the screen is rotated around the weighted handle 382, the marker surface 380 will rotate relative to the camera lens 386. Such relative movements between the marker surface 380 and the camera 386 are detected by processing software which recognises changes in the image on the marker surface 380 as viewed by the camera 386. The processing software makes consequential amendments to the orientation of the computer generated graphic displayed on the screen 312. The user is thereby given the impression that by rotating the handheld screen 310, the computer generated graphic is being controlled through their direct interaction with it, thereby providing a high level of immersion of the user with the content.

The mount 372 integrates the marker 378 and at least the lens of the camera 386 into a single enclosure or housing. This may provide two advantages. First, the marker image on the marker surface 380 is automatically maintained at or near the focal point of the camera 386. Secondly, the substantially closed, cowl-like, housing 372 removes the effects of external lighting conditions, ensuring the marker image is viewed in a constant or uniform light.

FIGS. 10 to 13 illustrate another embodiment of the motion sensor of FIGS. 8 and 9, suitable for use with a head mounted device 410. Typically, the device 410 is mounted on a pair of glasses worn by a user, the glasses having a display screen in front of each eye. The device 410 is provided with a removable marker mount 412 (shown more clearly in FIG. 13).

Different marker mounts 412 may be interchangeably attached to the device 410 to enable different images to be generated.

The detachable marker mount 412 has a cowl-like housing 414 having a recess 416 therein. When the marker mount 412 is attached to the head mounted device 410, the recess 416 clips onto a stud or boss 418 on the device 410. This retains the marker mount 412 securely on the device 410, but permits manual removal and replacement of the desired marker mount. Other mounting methods are also possible.

Figure 13:
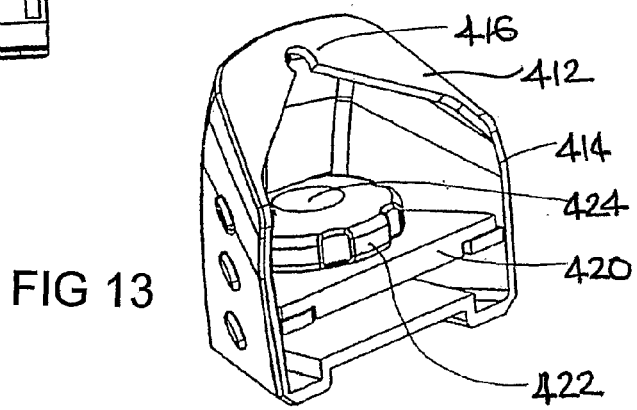
FIG. 13 is a perspective view of a marker mount used in the device of FIG. 10.
Figure 12:
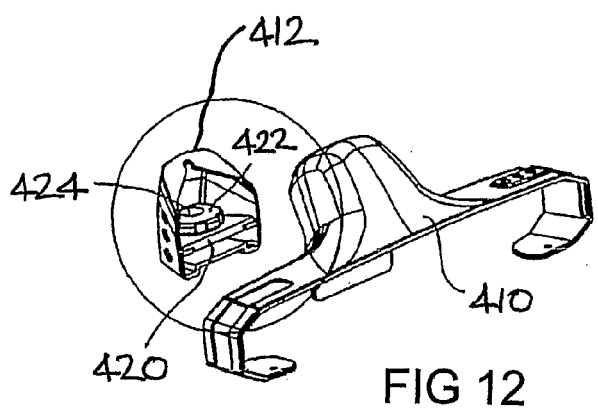
FIG. 12 is an exploded perspective view from the rear of the device of FIG. 10.

As shown more clearly in FIGS. 12 and 13, the marker mount 412 includes a support 420 in the form of a support plate having an aperture or bore therein. A marker element 422 is located in the aperture in the support plate 420. The marker element 422 has a neck portion located in or under the bore in the support 420 and a rounded head portion located at least partially above the bore. Preferably, the marker element 422 has its neck portion located in an oversized bore, the neck portion being surmounted by an enlarged head portion having a rounded underside to enable the neck portion to swing like a pendulum about at least two perpendicular axes. The marker element 422 is thereby supported in the support plate 420 in a gimbal-like arrangement, as described above with reference to the embodiment of FIGS. 8 and 9. Again, any other suitable mounting arrangement which allows the required freedom of movement of the marker element may be used.

The marker element 422 has a generally flat upper surface 424 which, in use, bears a unique image. The marker element 422 further comprises a lower weighted portion 426 which depends from the neck and head portions. As with the weighted handle 382 of the embodiment of FIGS. 8 and 9, the weighted portion 426 biases the marker element so that the marker surface 424 is maintained at a constant orientation, typically but not necessarily, a horizontal orientation.

The device 410 includes a camera support 428 for mounting a camera 430. The marker element and camera are spaced relative to each other so that the marker surface 424 is located at the focal point or region of the camera 430.

When the marker mount 412 is fitted to the device 410 worn on the head of a user, movement of the user's head, e.g. nodding, will cause relative movement between the marker surface 424 and the camera 430. In particular, the camera will move with the user's head but the marker element 424 will be biased by gravity to maintain a constant (vertical) orientation, by moving within the aperture in the support 420. These relative changes between camera and marker element are detected, and the computer generated image supplied to the glasses with which the device 410 is associated is modified accordingly.

The detachable marker mount 412 of FIGS. 10-13 has the advantages of the marker mount of the FIGS. 8 and 9 embodiment, and also has the advantage of being small and lightweight and able to be fitted to a head mounted display.

The device of FIGS. 8 and 9 or 10 to 13 allow for example a new page of a virtual book to be loaded onto a computer screen and then interacted with using a respective marker element. The user may for example rotate or zoom in or out of the image shown on the screen, by manipulating the handheld screen 310, or by using head movements if using a head mounted display and the movement device 410. The handheld screen apparatus and movement sensor or the head mounted display apparatus and movement sensor may be used to divert or distract a child's attention from a therapy which the child is receiving or pain which the child is experiencing.

Although the present invention has mainly been discussed above in relation to the provision of diversionary therapy, the devices themselves and their various features also have wider application, and may be used in general entertainment and gaming scenarios.

For example, a motion sensor using a camera and marker element that are mounted a fixed distance apart but are relatively movable in their orientation to one another, as shown in the embodiments of FIGS. 8 to 13 may be used as a general motion sensor with any device requiring motion sensing capabilities.

Further, the use of physical selector elements, e.g. a set of replaceable marker elements or artifacts, to act as physical menu elements could be used in many other areas also.

A handheld motion-sensitive display device including a camera for capturing images for providing additional interaction with the device besides the motion interaction is also useful generally.

It is to be understood that various alterations, additions and/or modifications may be made to the parts previously described without departing from the ambit of the present invention, and that, in the light of the above teachings, the present invention may be implemented in software, firmware and/or hardware in a variety of manners as would be understood by the skilled person.

EXAMPLES

A handheld storyboard motion-sensitive tablet device similar to that shown in FIG. 8 was used to investigate efficacy of such diversionary therapy devices as an adjunct to analgesia and sedation in children with acute burn injuries.

Phase One Trials

Forty-two children, undergoing a total of 56 dressing changes, were enrolled in this study. There were 29 males and 13 females with an age range of 3.5 to 14 years (median age 9 years). Total burns surface area was estimated from a paediatric Lund and Browder chart and ranged from 1 to 16% (median TBSA=5%). Patients were randomised into a treatment group (n=20 with a total of 24 dressing changes) and a control group (n=22 with 32 dressing changes). If a child required multiple dressing changes, they remained in their original study group. All dressing changes were carried out in the same treatment room. The treatment group used the hand held device both before and during the dressing change.

Basic multi-dimensional cognitive techniques, such as positive reinforcement, relaxation and an age appropriate video program were employed in the control group. No children were excluded on the basis of the site of their burn or impaired intellectual ability. Analgesic medications were administered prior to randomisation and all children received standard drug dosages, calculated on a dose per weight basis. The most frequently administered drugs were paracetamol/codeine or oxycodone. Other drugs administered included; oral midazolam, intravenous morphine and inhaled nitrous oxide.

Pulse rates (PR; beats per minute) and oxygen saturations (SaO2) on room air were recorded with a pulse oximeter. Respiratory rates (RR; breaths per minute) were also recorded. Pain scores were calculated using age appropriate clinically validated tools, enabling a standardised pain score from 0 to 5 to be recorded for each child. Pain scores for 3 to 4 year olds and non-verbalising children were calculated using the Faces, Legs, Activity, Cry and Consolability (FLACC) pain assessment tool. Pain scores for verbalising 4 to 8 year olds were measured with the Faces Pain Scale-Revised (FPS-R). Pain scores for 8 to 14 year olds were measured on a self-reporting Visual Analogue Scale (VAS).

All clinical measures recorded for an individual child were performed by the same investigator, who remained present for the entirety of the procedure. Clinical measures were recorded prior to the commencement of the dressing change, giving a baseline value. Subsequent recordings were taken at 10 minute intervals until the completion of the dressing.

Post-procedural clinical measures were also recorded 10 minutes after the completion of the dressing change. Clinical measure from the 10, 20 and 30 minute intervals were analysed. The parent or guardian, who accompanied the child during the dressing change, was then asked to score their child's overall level of pain during the procedure on a visual analogue scale (VAS 0-5).

The storyboard tablet device used consisted of a 7 inch LCD screen, measuring 300×200×500 millimetres, weighing 1000 grams and capable of a 600×800 resolution. The device required a connection to an Intel Pentium™ 4 computer with; 3.00 GHz; 2 GB RAM; NVIDIA Deforce 6800TTM graphics card. The system operated by inserting plastic figures into a camera unit mounted on the screen. The figurines had an icon on the top which was picked up by the camera unit and resulted in the animation of a 3-dimensional character. By manipulating the figure within the camera unit, a child could visualize the character from multiple angles. An audio narration prompted the child to perform tasks and move onto the next figure animation by selecting a new figure. A parent or care giver could follow the story and prompt the child with an accompanying story book.

A standard t-test was applied to each cohort of clinical measures from the two study groups and to parental pain evaluations. Patient pain scores, pulse rates, respiratory rates and oxygen saturations were analysed by comparing interval values to pre-procedural measures. The standard error of the mean (SEM) was calculated for interval measures.

There was no statistically significant difference between the treatment and control groups in age (p=0.397), total burns surface area (p=0.923) or pre-procedural pain scores (p=0.775). Pre-procedural clinical measures (PR, RR, SaO2 and pain scores) were not significantly different between the two study groups. The mean dressing times taken for each child also did not differ significantly between the two study groups (Control=34.1 minutes and treatment group=33.8 minutes; p=0.994). The sex distribution between the two study groups was: Treatment group 17/20 male and 3/20 female; and control group 13/22 male and 9/22 female. No child or parent reported any adverse effects from the use of the storyboard tablet device.

There was a significant reduction in patient pain in the treatment group compared to the control group at 10 minutes (p=0.015). This was repeated at the 30 minute interval (p=0.017). At the 20 minute mark, pain scores were reduced in the treatment group compared to control, but this failed to make statistical significance (p=0.08). Four patients underwent two separate dressing changes using the storyboard tablet device. There was no significant difference between pain scores at 10, 20, and 30 minutes for the two dressing changes, in these children.

The parent or guardian's assessment of their child's pain levels for the entire dressing change was significantly reduced in the treatment group compared to the control group (p=0.015).

The control population's respiratory rates (RR) were persistently elevated, when compared to pre-procedural rates at 10, 20 and 30 minute intervals. There was a significant reduction in RR's in the treatment group compared to the control group at 10 (p=0.005) and 20 (p=0.014) minutes. At 10 and 20 minutes, the treatment group's RR's were lower than the pre-procedural rate. At 30 minutes, the treatment group's RR's trended lower than the control's but this failed to make statistical significance (p=0.095) and was also slightly elevated compared to pre-procedural rates.

At 10 and 20 minutes both treatment and controls had elevated Pulse Rates compared to pre-procedural values. In the treatment group, the PR trended lower compared to the control group. This just failed to be statistically significant at 10 minutes (p=0.053) and was not significantly different at 20 minutes (p=0.24).

At 30 minutes, the control group showed a small drop in mean PR's compared to baseline values and the treatment group, a small rise but there was no statistical significance. PR's in the treatment group were persistently elevated by a small margin compared to pre-procedural levels. Across both study groups, PR'S showed the greatest individual variability and larger standard errors of the mean.

Oxygen saturations (SaO2) did not differ significantly in either the treatment or control groups in pre-procedural 10 minute interval or in the post-procedural groups.

The post-procedural clinical measures did not differ significantly from pre-procedural values in either the treatment or control groups.

The results of this study show that the use of this storyboard tablet device may significantly reduce patient pain scores in children undergoing burns dressing changes.

Pain scores were significantly lower at both of the 10 and 30 minute intervals. The reason for pain scores not being significantly reduced at the 20 minute interval was thought to be that the software program was designed to run for approximately 15 to 20 minutes. When children had completed their interactive tasks there was a brief delay so the system could be restarted, allowing the children to reuse the device and this would account for the significantly reduced pain scores being recorded at 30 minutes.

The mean dressing time in both groups was approximately 34 minutes. In both the treatment and control groups only 13/42 patients had data recorded at the 40 minute mark and it was felt that this would be an insignificant sample size to gather statistically valid data. In the treatment group 4/20 patients had two separate dressing changes in which the treatment device was used and there was no significant difference in their pain scores. These findings are consistent with previous smaller studies shown that the analgesic properties of virtual reality to not diminish with multiple treatments. Reducing patient pain, anxiety and therefore distress is especially significant for children who have to undergo multiple painful procedures because it could reduce avoidance behaviour and make the child more cooperative during subsequent treatments.

Parental pain scores were significantly lower in the treatment group. A care giver's behaviour and reaction to a procedure can have a major effect on the child's behaviours during a treatment. If the parent is more satisfied with their child's analgesia and anxiety during a procedure this can have a positive effect on the child both during the current and for future treatment sessions.

Respiratory rates are heavily influenced by negative emotions in children. The significant reduction seen in the treatment group's respiratory rates compared to the control not only reflects the lower pain scores but indicates a reduced association with negative emotions and the change of dressings. At 10 and 20 minutes, RR had fallen below the pre-procedural baseline average. Pre-procedural apprehension may account for the fall in RR's seen in the treatment group. The lack of significance observed at 30 minutes could be explained by children in both groups becoming more accepting of the treatment over time, more settled in their environment and by the fact that at 30 minutes, most dressing changes were nearing completion.

Pulse rates (PR) can be influenced by cognitive factors immediately prior to and at the commencement of a painful procedure. However there is a poor correlation between the PR and pain scores as the procedure continues. No significant difference in the PR was observed between the two study groups.

Oxygen saturations (SaO2) were not significantly different in either group at any of the measurement intervals. SaO2 is dependent on physiological lung function and does not appear to be affected by pain or psychological factors in this clinical setting. No child in this study was pharmacologically sedated sufficiently to affect ventilation and SaO2.

Phase Two

Twenty one children having burn dressing changes in an outpatients department were enrolled. A standard pre-medication of 0.15 mg/kg of Oxycodone was administered, and the children were randomised into a treatment group of ten and a control group of eleven.

Pulse and respiratory rates and oxygen saturations were recorded at 5 minutes pre and post procedurally and at 10 minute intervals during dressing changes.

Pain scores were recorded at the same intervals with the Wong-Baker faces scale (4-7 years) or an Analogue scale (7-14 years) to a score from 0 to 5.

There was no significant difference between the two groups in age, sex or total burns surface area, and no significant difference in oxycodone doses between the study groups.

Figure 14:
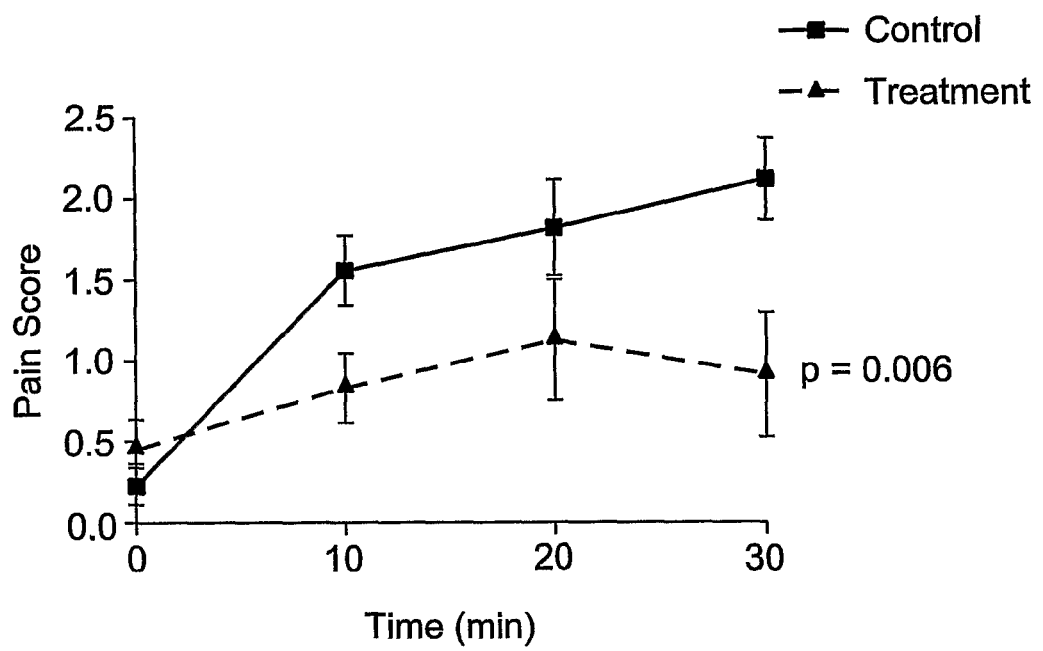
FIG. 14 is a table of pain score against time for a trial of paediatric burns victims, showing data for a group treated using a diversionary therapy device according to an embodiment of the invention and for a control group.
Figure 15:
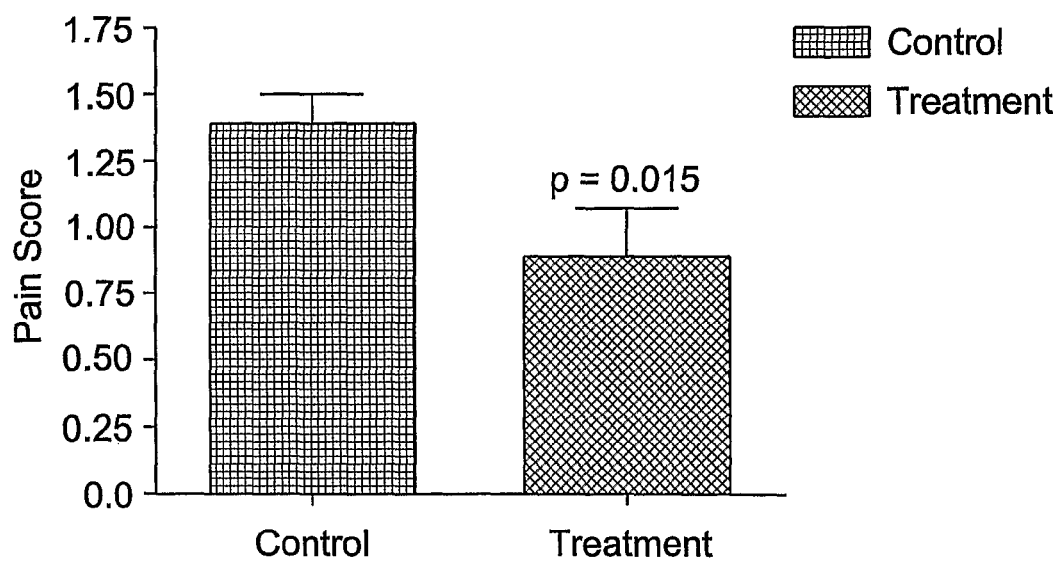
FIG. 15 is a parental pain assessment score for the two groups of FIG. 13.

There was significant reduction in reported pain scores by children and by their parents in the storyboard tablet device group, as shown in FIGS. 14 and 15

Both trials show that the storyboard motion-sensitive tablet device may be a useful adjunct to pharmacological analgesia.

The invention claimed is:

1. A method of providing diversionary therapy to a patient during a treatment using a device having a display screen which displays digital content relating to a three-dimensional environment, the method including the steps of:
monitoring movement of the device produced by the patient; and
altering the digital content displayed on the screen based on the monitored movement of the device,
wherein the patient is able to interact with the three-dimensional environment by moving the device, the interaction providing a distraction to the patient from the treatment; and
wherein the device has a pair of opposed handgrips on the housing which are oriented along an axis skew to an axis dividing upper and lower regions of the display screen whereby said skew orientation of the handgrips prompts the patient to immediately rotate the device thereby causing movement which alters the digital content.

2. The method of claim 1, wherein the device includes a set of selector elements that are interchangeably mountable on the device to make selections, the method including the step of:
altering the digital content displayed on the screen based on selections made by the patient using the selector elements.

3. The method of claim 1, wherein the device includes a touch screen, the method including the step of:
altering the digital content displayed on the screen in response to the patient touching the touch screen.

4. The method according to claim 1, wherein the device includes one or more output devices, each output device being a vibrational element or a sound generator, the method including the step of:
providing an output from the one or more output devices in accordance with patient interaction.

5. The method of claim 1, wherein the device has a link for communication between the device and an external device, the method including one or both of the steps of:
receiving digital content and processing other functionality from the external device.

6. The method of claim 1, wherein the device includes a physiological sensor, the method including the steps of:
receiving a monitored condition of the patient from the physiological sensor; and
using the monitored condition to provide a patient-device interaction.

7. The method of claim 1, wherein the device is a tablet device.

8. The method of claim 1, wherein the device is a head mountable device.

9. A diversionary therapy apparatus including:
a tablet device configured to be held and moved by a patient during a treatment; and
a set of interchangeable physical selector elements for mounting on the tablet device;
the tablet device having a housing in which are mounted: a display screen for displaying digital content;
a motion sensor for sensing movement of the tablet device; and
a controller for determining movement of the tablet device through the motion sensor and for displaying digital content on the screen in accordance with the tablet device movement, the digital content defining a three-dimensional environment, the controller allowing the patient to interact with the three-dimensional environment by movement of the tablet device;
the controller further determining which selector element is mounted on the tablet device, and altering the digital content according to the determination;
wherein the device further includes a pair of opposing handgrips on the housing which are oriented along an axis skew to an axis dividing the upper and lower regions of the display screen, and wherein said skew orientation of the handgrips prompts the patient to immediately rotate the device thereby causing movement which alters the digital content.

10. The apparatus of claim 9, wherein the housing is waterproof.

11. The apparatus of claim 9, wherein the tablet device includes a domed portion on a rear surface of the tablet device for supporting the tablet device during movement.

12. The apparatus of claim 9 wherein the tablet device includes at least one of a touch screen, a sound sensor, a sound generator, a vibrational motor and a physiological sensor.

13. A method of providing diversionary therapy, the method including the step of:
providing a patient with apparatus as claimed in claim 9; and
allowing the patient to operate the apparatus during a treatment.

14. A tablet device forming part of a diversionary therapy apparatus and intended for use with a set of interchangeable physical selector elements for mounting on the tablet device; the tablet device having a housing in which are mounted:
a display screen for displaying digital content;
a motion sensor for sensing movement of the tablet device; and
a controller for determining movement of the tablet device through the motion sensor and for displaying digital content on the screen in accordance with the tablet device movement, the digital content defining a three-dimensional environment, the controller allowing the patient to interact with the three-dimensional environment by movement of the tablet device;

the controller further determining which selector element is mounted on the tablet device, and altering the digital content according to the determination, wherein the tablet device further includes a pair of opposing handgrips on the housing which are oriented along an axis skew to an axis dividing the upper and lower regions of the display screen, and wherein said skew orientation of the handgrips prompts the patient to immediately rotate the device thereby causing movement which alters the digital content.

15. A diversionary therapy apparatus including a tablet device configured to be held and moved by a patient during a treatment, the tablet device having a housing in which are mounted:

a display screen for displaying digital content;

a motion sensor for sensing movement of the tablet device;

a controller for determining movement of the tablet device through the motion sensor and for displaying digital content on the screen in accordance with the tablet device movement, the digital content defining a three-dimensional environment, the controller allowing the patient to interact with the three-dimensional environment by movement of the tablet device, the controller further determining which selector element is mounted on the tablet device, and altering the digital content according to the determination; and a pair of opposing handgrips on the housing which are oriented along an axis skew to an axis dividing the upper and lower regions of the display screen, and wherein said skew orientation of the hand grips prompts the patient to immediately rotate the device thereby causing movement which alters the digital content.

16. A diversionary therapy apparatus including a tablet device configured to be held and moved by a patient during a treatment, the tablet device having:

a housing in which are mounted:

a display screen for displaying digital content;

a motion sensor for sensing movement of the tablet device; and a controller for determining movement of the tablet device through the motion sensor and for displaying digital content on the screen in accordance with the tablet device movement, the digital content defining a three-dimensional environment, the controller allowing the patient to interact with the three-dimensional environment by movement of the tablet device, the controller further determining which selector element is mounted on the tablet device, and altering the digital content according to the determination; and a pair of handgrips on the housing, the handgrips being provided along an axis skew to an axis dividing upper and lower regions of the display screen.

* * * * *